United States Patent
Hotta et al.

(10) Patent No.: US 6,660,145 B2
(45) Date of Patent: Dec. 9, 2003

(54) OXYGEN SENSOR ELEMENT

(75) Inventors: Yasumichi Hotta, Mie-ken (JP); Hiroshi Sugino, Aichi-ken (JP); Tooru Katafuchi, Kariya (JP); Namitsugu Fujii, Yokkaichi (JP)

(73) Assignee: Denso Corporation, Kariya (JP)

( * ) Notice: Subject to any disclaimer, the term of this patent is extended or adjusted under 35 U.S.C. 154(b) by 34 days.

(21) Appl. No.: 09/960,980

(22) Filed: Sep. 25, 2001

(65) Prior Publication Data
US 2002/0060152 A1 May 23, 2002

(30) Foreign Application Priority Data

Oct. 5, 2000 (JP) .......................... 2000-306575
Aug. 1, 2001 (JP) .......................... 2001-234062

(51) Int. Cl.⁷ ................................... G01N 27/407
(52) U.S. Cl. ............................. 204/429; 204/427
(58) Field of Search ........................ 204/421–429

(56) References Cited

U.S. PATENT DOCUMENTS 4,021,326 A * 5/1977 Pollner et al.
4,272,349 A * 6/1981 Furutani et al.
5,423,973 A * 6/1995 Friese et al.
5,443,711 A   8/1995 Kojima et al.
5,472,591 A   12/1995 Saito et al.
5,716,507 A * 2/1998 Tanaka et al.

FOREIGN PATENT DOCUMENTS

JP   1-203963   8/1989
JP   2-151755   9/1990
JP   7-134114   5/1995

* cited by examiner

Primary Examiner—T. Tung
(74) Attorney, Agent, or Firm—Nixon & Vanderhye P.C.

(57) ABSTRACT

An oxygen sensor element is provided which may be used in an oxygen sensor designed to measure the concentration of oxygen contained in exhaust gasses of an automotive internal combustion engine. The gas sensor element includes a solid electrolyte body, a target gas electrode, a reference gas electrode, and a catalytic layer formed over the target gas electrode. The catalytic layer is made of heat resisting ceramic grains which hold thereon catalytic metal grains whose average grain size is 0.3 to 2.0 $\mu$m, a weight of catalytic metal grains per unit area of the catalytic layer, as defined by projecting the target gas electrode on a plane, is 10 to 200 $\mu g/cm^2$. This facilitates the reaction of exhaust gasses such as $H_2$, $NOx$, and $HC$ with $O_2$ over the target gas electrode, thus resulting in improved accuracy of a sensor output over a wide temperature range.

12 Claims, 3 Drawing Sheets

OXYGEN SENSOR ELEMENT

BACKGROUND OF THE INVENTION

1. Technical Field of the Invention

The present invention relates generally to a sensor element of an oxygen sensor which may be employed in air-fuel ratio control of internal combustion engines, and more particularly to an improved internal structure of such a sensor element which is designed to produce a sensor output accurately at a quick response rate.

2. Background Art

There are used oxygen sensors for controlling the air-fuel ratio of a mixture supplied to an internal combustion engine of an automotive vehicle. This type of oxygen sensor is usually disposed in an exhaust system of the engine to measure the concentration of oxygen contained in exhaust gasses and includes a sensor element which consists essentially of a solid electrolyte body, a target gas electrode, and a reference gas electrode.

The target gas electrode is disposed within a gas chamber filled with a gas to be measured. The target gas electrode is covered with a porous protective layer made of $MgO.Al_2O_3$. The reference gas electrode is disposed in a reference gas chamber. The solid electrolyte body is usually made of an oxygen ion conductive material such as a zirconia-based ceramic material. The solid electrolyte body works to produce the electromotive force as a function of the concentration of oxygen contained in the gasses and outputs a sensor signal through the target gas electrode and the reference gas electrode.

In recent years, the emission regulations have been made more rigorous. In order to meet this requirement, the improvement of accuracy and durability of the above oxygen sensor is sought for enhancing the burning efficiency of the engine. The oxygen sensor element are, therefore, required to output a sensor signal accurately at a quick response rate over a wide temperature range. The oxygen sensor element is, as described above, designed as a concentration cell which produces the electromotive force as a function of a difference between concentrations of oxygen contained in gasses to which the target gas and reference gas electrodes are exposed, respectively. The target gas electrode and the reference gas electrode are each made of platinum exhibiting the catalysis so as to produce the electromotive force which changes greatly across the concentration of oxygen corresponding to the stoichiometric air-fuel ratio (i.e., an excess coefficient or air ratio $\lambda=1$). Producing a sensor signal accurately at a quick response rate in this type of oxygen sensor element requires a decreased shift in $\lambda$-point at which the electromotive force indicates the air ratio $\lambda=1$.

In order to realize such an oxygen sensor element, Japanese Patent First Publication No. 2-1511755 (corresponding to U.S. Pat. No. 5,443,711) and Japanese Patent First Publication No. 1-203963 propose the formation of a catalytic layer on the target gas electrode for minimizing the shift in $\lambda$-point. The catalytic layer is made of a carrier which is formed by a nonstoichiometric compound of a transition metal oxide such as $TiO_2$ and has catalytic metal grains held therein. The oxygen sensor elements as taught in the above publications, however, lack the stability of operation over a wide environmental range and has a difficulty in decreasing the $\lambda$-point sufficiently.

SUMMARY OF THE INVENTION

It is therefore a principal object of the invention to avoid the disadvantages of the prior art.

It is another object of the invention to provide an oxygen sensor element which is designed to produce a sensor output accurately over a wide temperature range and a manufacturing method thereof.

According to one aspect of the invention, there is provided an oxygen sensor element which comprises: (a) an oxygen ion conductive solid electrolyte body; (b) a target gas electrode provided on a surface of the solid electrolyte body so as to be exposed to a gas to be measured; (c) a reference gas electrode provided on a surface of the solid electrolyte body so as to be exposed to a reference gas; (d) an electrode protective layer provided to cover the target gas electrode, the electrode protective layer having a porosity of 6 to 30% and a thickness of 70 to 500 $\mu$m; (e) a catalytic layer provided to cover the electrode protective layer, the catalytic layer being made of heat resisting ceramic grains which hold therein catalytic metal grains whose average grain size is 0.3 to 2.0 $\mu$m, a weight of catalytic metal grains per unit area of the catalytic layer, as defined by projecting the target gas electrode on a plane, is 10 to 200 $\mu g/cm^2$; and (f) a catalytic protective layer provided to cover the catalytic layer.

In the preferred mode of the invention, the catalytic layer has a porosity of 20 to 60% and a thickness of 20 to 150 $\mu$m.

The catalytic metal grains may be made from at least one of Pt, Pd, Rh, and Ru.

The electrode protective layer may have a porosity of 6 to 15% and a thickness of 100 to 250 $\mu$m.

The electrode protective layer is formed by a heat resisting metallic oxide made of at least one of alumina, alumina.magnesia spinel, and zirconia.

The catalytic protective layer may have a porosity of 30 to 60% and a thickness of 20 to 150 $\mu$m.

According to the second aspect of the invention, there is provided an oxygen sensor element which comprises: (a) an oxygen ion conductive solid electrolyte body; (b) a target gas electrode provided on a surface of the solid electrolyte body so as to be exposed to a gas to be measured; (c) a reference gas electrode provided on a surface of the solid electrolyte body so as to be exposed to a reference gas; (d) an electrode protective layer provided to cover the target gas electrode; (e) a catalytic layer provided to cover the electrode protective layer, the catalytic layer being made of heat resisting ceramic grains which hold therein catalytic metal grains whose average grain size is 0.3 to 2.0 $\mu$m, a weight of catalytic metal grains per unit area of the catalytic layer, as defined by projecting the target gas electrode on a plane, is 10 to 200 $\mu g/cm^2$, the heat resisting ceramic grains being each made of $Al_2O_3$ which has at least one of a $\gamma$-phase and a $\theta$-phase in crystal structure and to which $La_2O_3$ is added, a specific surface of the heat resisting ceramic gains being 50 to 200 $m^2/g$; (f) a catalytic protective layer provided to cover the catalytic layer.

In the preferred mode of the invention, an added quantity of $La_2O_3$ is 0.5 to 5 mol % for total 100 mol % of $Al_2O_3$ and $La_2O_3$.

The catalytic layer has a porosity of 20 to 60% and a thickness of 20 to 150 $\mu$m.

The catalytic metal grains may be made from at least one of Pt, Pd, Rh, and Ru.

The electrode protective layer has a porosity of 6 to 15% and a thickness of 100 to 250 $\mu$m.

The electrode protective layer is formed by a heat resisting metallic oxide made of at least one of alumina, alumina-magnesia spinel, and zirconia.

The catalytic protective layer has a porosity of 30 to 60% and a thickness of 20 to 150 μm.

According to the third aspect of the invention, there is provided a method of producing an oxygen sensor element which comprises the steps of: (a) preparing an oxygen ion conductive solid electrolyte body on which a target gas electrode is provided so as to be exposed to a gas to be measured and a reference gas electrode provided so as to be exposed to a reference gas; (b) forming an electrode protective layer on the target gas electrode; and (c) forming a catalytic layer on the electrode protective layer by dipping heat resisting ceramic particles in a solution of a catalytic metal grain-forming material to stick catalytic metal salt to the heat resisting ceramic particles, subjecting the heat resisting ceramic particles to heat treatment at 900 to 1200° C. to deposit catalytic metal grains on the heat resisting ceramic particles, adding an inorganic binder and a solvent to the heat resisting ceramic particles to produce slurry, applying the slurry to a surface of the electrode protective layer, and subjecting the slurry to heat treatment at 500 to 1000° C.

In the preferred mode of the invention, the electrode protective layer is made by plasma-spraying heat resisting metallic oxide particles over the target gas electrode.

The electrode protective layer may alternatively be made by applying an electrode protective layer-forming material containing heat resisting metallic oxide powders to a surface of the target gas electrode and baking the electrode protective layer-forming material.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
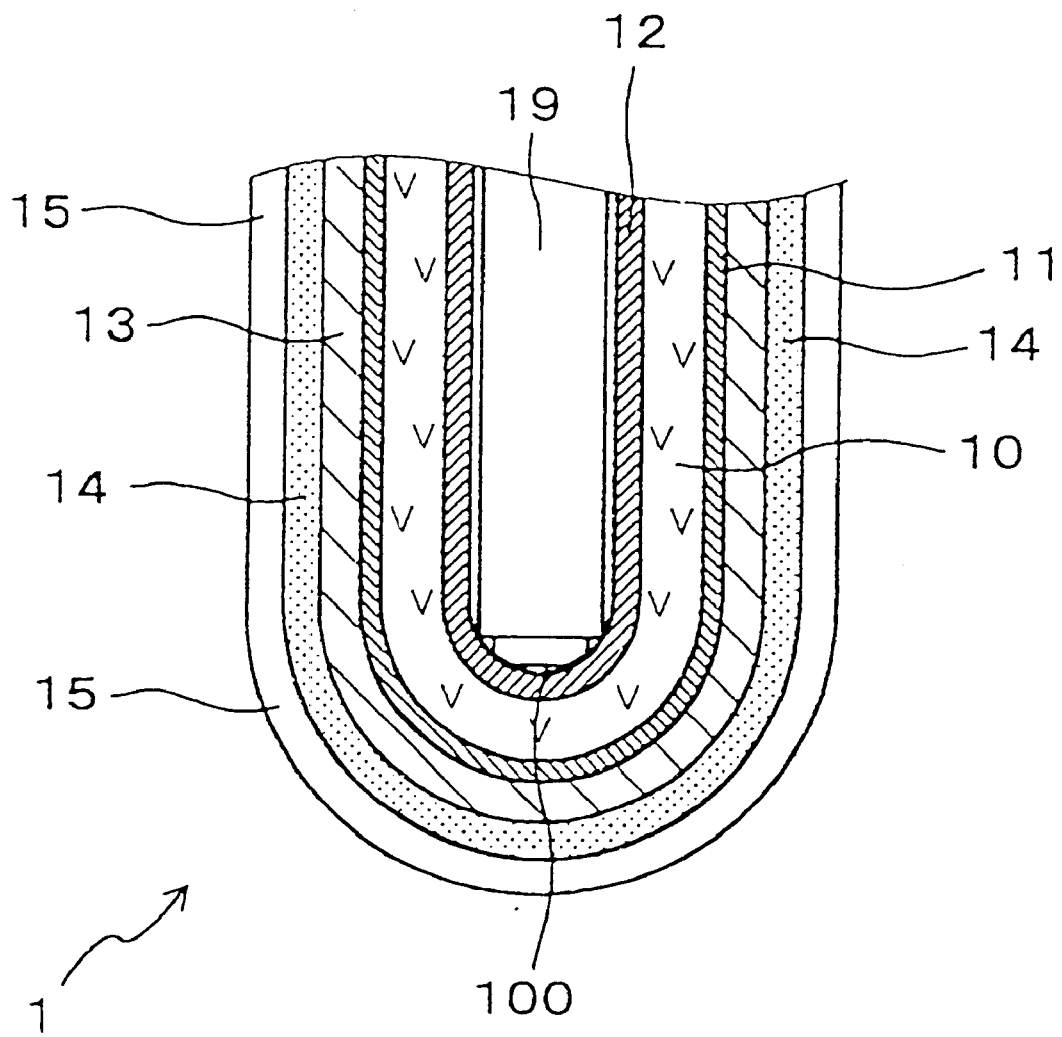
FIG. 1 is a partially sectional view which shows an oxygen sensor element according to the invention.

Referring to the drawings, wherein like reference numbers refer to like parts in several views, particularly to FIG. 1 and, there is shown an oxygen sensor element 1 according to the invention.

The oxygen sensor element 1, like the conventional one discussed in the introductory part of this application, works as a concentration cell and consists essentially of a hollow solid electrolyte body 10 having oxygen ion conductivity, a target gas electrode 11, and a reference gas electrode 12. The target gas electrode 11 is formed on an outer surface of the solid electrolyte body 10 and to be exposed to a gas to be measured. The reference gas electrode 12 is formed on an inner surface of the solid electrolyte body 10 and to be exposed to a reference gas such as air.

Figure 2A:
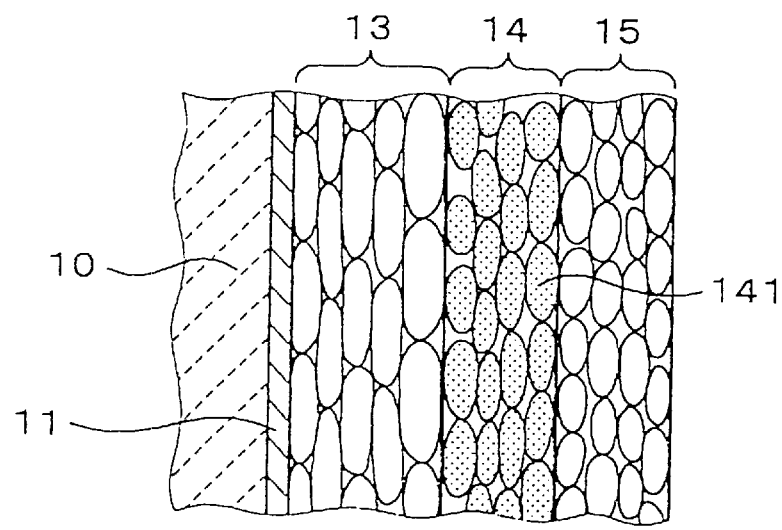
FIG. 2(a) is a partially enlarged sectional view which shows an electrode protective layer, a catalytic layer, and a catalytic protective layer formed on a target gas electrode of an oxygen sensor element.
Figure 2B:
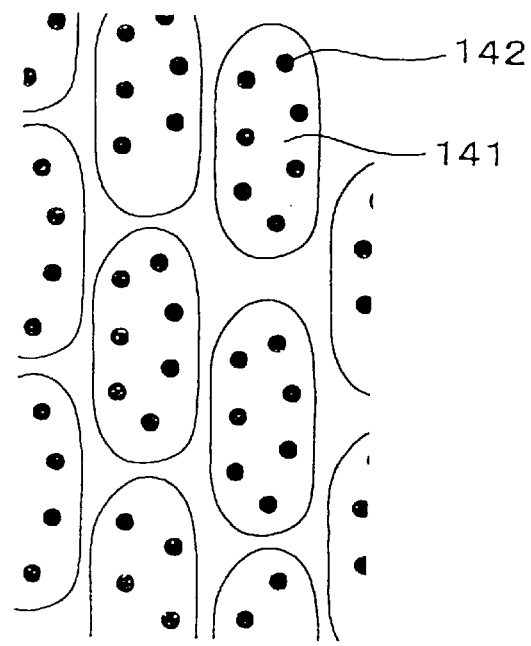
FIG. 2(b) is a partially enlarged sectional view which shows an internal structure of a catalytic layer.

The target gas electrode 11 has formed thereon an electrode protective layer 13 which is covered with catalytic layer 14 and a catalytic protective layer 15. The catalytic layer 14 is, as clearly shown in FIG. 2(b), made up of heat resisting ceramic grains 141 each holding catalytic metal grains 142 thereon. The average grain size of the catalytic metal grains 142 is so adjusted as to fall within a range of 0.3 to 2.0 μm. Additionally, the weight of the catalytic metal grains 142 per unit area of the catalytic layer 14, as defined by projecting the target gas electrode 11 on a plane, is so adjusted as to fall within a range of 10 to 200 μg/cm$^2$.

Figure 3:
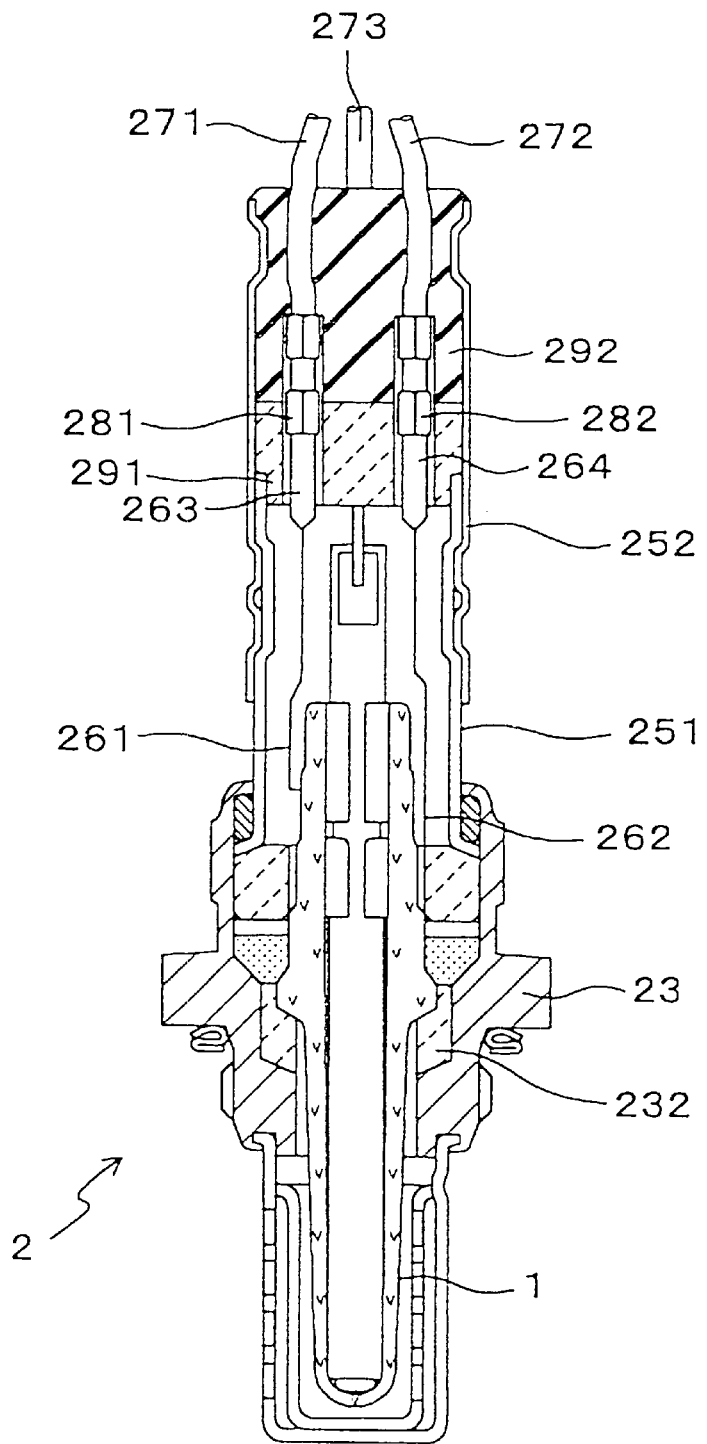
FIG. 3 is a longitudinally sectional view which shows an oxygen sensor equipped with the oxygen sensor element of FIG. 1.

The oxygen sensor element 1 may be installed in an oxygen sensor 2, as shown in FIG. 3, which is to be disposed in an exhaust pipe of an internal combustion engine of an automotive vehicle to measure the oxygen content of exhaust gasses for engine burning control.

Referring back to FIG. 1, the solid electrolyte body 10 is of a cylindrical cup-shape and has formed therein a reference gas chamber 100 filled with air as the reference gas. Within the reference gas chamber 100, a ceramic bar heater 19 is disposed which heats the oxygen sensor element 1 up to a suitable temperature for measuring the concentration of oxygen. The heater 19 is retained within the reference gas chamber 100 with a given gap between itself and an inner wall of the oxygen sensor element 1 (i.e., the reference gas electrode 12) and has a head contact with the inner wall of the oxygen sensor element 1.

The target gas electrode 11 is, as described above, covered with the electrode protective layer 13, the catalytic layer 14, and the catalytic protective layer 15. In FIG. 1, these layers are scaled up for ease of visibility of illustration. The oxygen sensor element 1 has lead electrodes and terminal electrodes (not shown) formed in the outer and inner surfaces thereof which are electrically connected to the target gas electrode 11 and the reference gas electrode 12 for applying the voltage thereto.

The solid electrolyte body 10 is made of an oxygen ion conductive zirconia. The target gas electrode 11 and the reference gas electrode 12 are each made of a baked platinum electrode. The electrode protective layer 13 is made of a $MgO.Al_2O_3$ spinel. The electrode protective layer 13 may alternatively be made of a heat resisting metallic oxide such as alumina, zirconia, or a combination thereof including the $MgO.Al_2O_3$ spinel. The catalytic layer 14 is made up of the heat resisting grains 141 and the catalytic metal grains 142. The heat resisting grains 141 are formed by γ-phase $Al_2O_3$ particles to which $La_2O_3$ is added. The catalytic metal grains 142 are made of platinum-rhodium and carried on each of the γ-phase $Al_2O_3$ particles. The catalytic protective layer 15 is made of γphase $Al_2O_3$. The heat resisting gains 141 may alternatively made of θ-phase $Al_2O_3$ particles or a combination of γ-phase $Al_2O_3$ particle and θ-phase $Al_2O_3$ particles. The catalytic metal grains 142 may alternatively be made of at least one of Pt, Pd, Rh, and Ru which are excellent in catalysis.

The production of the gas sensor element 1 is accomplished in the following steps.

First, grains are made which contain 5 mol % of $Y_2O_3$ and $ZrO_2$ and compressed to a cup-shape, as shown FIG. 1, after which it is baked at 1400 to 1600° C. in an electric furnace to form the solid electrolyte body 10.

An outer wall of the solid electrolyte body 10 is chemically plated or deposited with platinum to form the target gas electrode 11.

Similarly, an inner wall of the solid electrolyte body 10 is chemically plated with platinum to form the reference gas electrode 12.

$MgO.Al_2O_3$ spinel powders are plasma-sprayed over the surface of the target gas electrode 11 to form the electrode protective layer 13. The electrode protective layer 13 may alternatively be formed by alumina, zirconia, or a combination thereof including the $MgO.Al_2O_3$ spinel using plasma-spraying techniques. Instead of the plasma-spraying techniques, paste-printing or baking techniques or a green sheet may be employed. For example, the formation of the electrode protective layer 13 may be accomplished by applying an electrode protective layer-forming material containing heat resisting metallic oxide powders to a surface of the target gas electrode 11 and baking it.

The catalytic layer 14 is formed over the surface of the electrode protective layer 13 in the following steps.

First, γ-phase $Al_2O_3$ particles to which $La_2O_3$ is added and whose average grain size is 4 μm and specific surface area is between 50 and 200 $m^2/g$, e.g., 100 $m^2/g$ are prepared. If the specific surface area is less than 50 $m^2/g$, it may cause the catalysis of the catalytic metal grains 142 to be insufficient for inducing reaction of $H_2$, NOx, and HC with $O_2$. Alternatively, if the specific surface area is greater than 200 $m^2/g$, it may cause the specific surface to be decreased by long exposure to high temperatures, thus resulting in decrease in catalysis of the catalytic layer 14. θ-phase $Al_2O_3$ particles or a combination of γ-phase $Al_2O_3$ particles and θ-phase $Al_2O_3$ particles may alternatively be used. The amount of $La_2O_3$ is preferably 0.5 to 5 mol % for total 100 mol % of $Al_2O_3$ and $La_2O_3$. This enhances the thermal stability of θ- or γ-phase of the $Al_2O_3$ particles.

The $Al_2O_3$ particles are dipped in solution of a catalytic metal grain-forming material made of platinum-rhodium. This causes catalytic metal salt to be stuck to the $Al_2O_3$ particles.

The $Al_2O_3$ particles are subjected to heat treatment at 900 to 1200° C., e.g., 1000° C. for one hour to deposit and grow platinum-rhodium particles (i.e., catalytic metal grains) on the $Al_2O_3$ particles. This produces the λ-phase $Al_2O_3$ particles on which the platinum-rhodium particles whose average grain size is 0.5 μm are formed. The solid ratio of the platinum-rhodium particles to the $Al_2O_3$ particles is 0.5 wt %.

Next, alumina sol and/or aluminum nitrate is added as binder to the λ-phase $Al_2O_3$ particles, thereby producing slurry using a solvent of water. The slurry is applied to the surface of the electrode protective layer 13.

Finally, the slurry formed on the electrode protective layer 13 is dried and subjected to heat treatment at 500 to 1000° C. to form the catalytic layer 14 which has a thickness of 60 μm and a porosity of 40%. The thickness may lie within a range of 20 to 150 μm, and the porosity may lie within a range of 20 to 60% in light of the degree of diffusion and reaction of gasses within the catalytic layer 14.

After the formation of the catalytic layer 14 on the electrode protective layer 13, the catalytic protective layer 15 is formed on the catalytic layer 14 in the following manner.

First, the same slurry as that used to form the catalytic layer 14 is prepared.

Next, the slurry is applied to the surface of the catalytic layer 14 and then subjected to heat treatment to form the catalytic protective layer 15 which has a thickness of 60 μm and a porosity of 50%. The porosity may lie within a range of 30 to 60%, and the thickness may lie within a range of 20 to 150 μm for keeping the catalysis of the catalytic layer 14 even in an atmosphere where a poisonous substance such as Si exists.

The oxygen sensor 2 includes, as shown in FIG. 3, a hollow cylindrical metal housing 23 within which the oxygen sensor element 1 is retained through a hollow cylindrical insulator 232, an air cover 251, a connector cover 252, and a protective cover assembly 50 consisting of an outer and an inner cover. The air cover 251 is installed in a base end of the housing 23. The connector cover 252 which surrounds an insulation porcelain 291 and an insulating elastic member 292 made of, for example, rubber is joined to an end of the air cover 251.

The protective cover assembly 50 is installed on a head of the housing 23 to define a gas chamber into which a gas to be measured is admitted through gas holes formed in the outer and inner covers.

The elastic member 292 retains therein sensor output leads 271 and 272 and a pair of heater leads 273 (only one is shown for the brevity of illustration). The sensor output leads 271 and 272 are connected electrically to the oxygen sensor element 1 through connectors 281 and 282 coupled with terminals 263 and 264 installed on the oxygen sensor element 1 for applying the voltage to and picking up a sensor signal from the oxygen sensor element 1. The leads 273 are connected to the heater 19 for power supply. For a more detailed structure and operation of the oxygen sensor 2, reference is made to U.S. Pat. No. 6,222,372 B1 issued on Apr. 24, 2001, assigned to the same assignee as that of this application, disclosure of which is incorporated herein by reference.

We measured shifts in λ-point (i.e., a difference between a correct sensor output indicating an excess coefficient or air ratio λ=1, as discussed in the introductory part of this application, and an actual sensor output) in terms of different combinations of the grain size and weight of the catalytic metal grains 142.

Ten test samples No. 1 to No. 10 of the oxygen sensor element 1, as shown in table 1, were prepared.

The grain size of the catalytic metal grains 142 of each test sample was adjusted by changing the temperature at which the catalytic metal grains 142 were held in the ceramic grains 141 in the heat treatment.

The weight of the catalytic metal grains 141 per unit area of the ceramic grains 141 of each test sample was adjusted by changing the number of the catalytic metal grains 142 held in the ceramic grains 141.

The measurement of the weight of the catalytic metal grains 142 were made in the following manner.

First, the catalytic metal grains 142 held in the catalytic layer 14 of each test sample was dissolved in aqua regia and measured in weight using the atomic absorption method.

The outer surface of the target gas electrode 11 was assumed to be level and measured in area. Using this data, the weight of the catalytic metal grains 142 per unit area of the target gas electrode 11 was determined.

The shifts in λ-point of each test sample were measured before and after a durability test in which the test sample was installed in an exhaust pipe of a 300 cc internal combustion engine of an automotive vehicle and exposed to exhaust gasses at 850 to 950° C. for 1000 hours.

The measurement of the shift in λ-point is accomplished by exposing each test sample to exhaust gasses at 600° C.

while running the engine under feedback control using an output of the test sample, measuring concentrations of all the exhaust gasses except oxygen using a gas analyzer to estimate the correct concentration of oxygen, and determining the air ratio $\lambda$. The test samples showing the air ratio $\lambda=1\pm0.002$ were decided to be good, as listed in table 1, while the test samples showing the air ratio $\lambda<0.998$ or $>1.002$ were decided to be no good.

TABLE 1

| No. | Grain size ($\mu$m) | Weight ($\mu$g/cm$^2$) | Shift in $\lambda$-point | |
|---|---|---|---|---|
| | | | Before durability text | After durability test |
| 1 | 0.1 | 50 | NG | NG |
| 2 | 0.3 | 50 | OK | OK |
| 3 | 0.5 | 5 | OK | NG |
| 4 | 0.5 | 10 | OK | OK |
| 5 | 0.5 | 50 | OK | OK |
| 6 | 0.5 | 200 | OK | OK |
| 7 | 0.5 | 300 | NG | NG |
| 8 | 1 | 50 | OK | OK |
| 9 | 2 | 100 | OK | OK |
| 10 | 5 | 100 | NG | NG |

The table 1 shows that the test samples Nos. 2, 4, 5, 6, 8, and 9, in which the average grain size of the catalytic metal grains 142 lies within a range of 0.3 to 2 $\mu$m, and the weight of the catalytic metal grains 142 per unit area of the target gas electrode 11 lies within a range of 10 to 200 $\mu$g/cm$^2$, are permissible in the shift in $\lambda$-point. It is found that the average grain size of 0.3 $\mu$m or more serves to minimize a change in grain size after the durability test and keep the catalysis of the catalytic layer 14.

The test samples Nos. 1 and 7, in which the average grain size of the catalytic metal grains 142 is smaller than 0.3 $\mu$m, and the weight of the catalytic metal grains 142 per unit area of the target gas electrode 11 is greater than 200 $\mu$g/cm$^2$, showed great shifts in $\lambda$-point before undergoing the durability test. This would be because a ratio of a rich-to-lean response time to a lean-to-rich response time of each of the test samples Nos. 1 and 7 during the feedback control of the engine became great on account of the absorption of the gasses into the catalytic layer 14.

The test samples Nos. 3 and 10, in which the average grain size of the catalytic metal grains 142 is greater than 2 $\mu$m, and the weight of the catalytic metal grains 142 per unit area of the target gas electrode 11 is smaller than 10 $\mu$g/cm$^2$, showed great shifts in $\lambda$-point both before and after the durability test. This would be because the catalysis of the catalytic layer 14 were insufficient for burning H$_2$ and NOx.

Specifically, the formation of the catalytic layer 14 on the electrode protective layer 13 which is made of the ceramic grains 141 each holding therein the catalytic metal grains 142 whose average grain size lies within a range of 0.3 to 2.0 $\mu$m and weight per unit area of the target gas electrode 11 lies within a range of 10 to 200 $\mu$g/cm$^2$ enables exhaust gasses such as H$_2$, NOx, and HC to be burnt sufficiently over a wide temperature range and provides the ease of absorption and release of the oxygen gas into and from the catalytic metal grains 142. This provides a good balance between the rich-to-lean response time and the lean-to-rich response time of the oxygen sensor element 1 during feedback control of the engine using an output of the oxygen sensor element 1.

The second embodiment will be described below which is different from the first embodiment only in porosity and thickness of the electrode protective layer 13. Other arrangements are identical, and explanation thereof in detail will be omitted here.

We measured the shifts in $\lambda$-point in terms of different combinations of the porosity and thickness of the electrode protective layer 13.

Ten test samples No. 11 to No. 20 of the oxygen sensor element 1, as shown in table 2, were prepared.

The porosity of the electrode protective layer 13 of each test sample was adjusted by changing the grain size of MgO.Al$_2$O$_3$ spinel powders to be plasma-sprayed over the surface of the target gas electrode 11 to form the electrode protective layer 13 and plasma-spraying conditions. The thickness of the electrode protective layer 13 was adjusted by changing the plasma-spraying conditions.

The shifts in $\lambda$-point of each test sample were measured to evaluate the test sample in the same manner as in the first embodiment.

TABLE 2

| | Electrode protective layer | | Shift in $\lambda$-point | |
|---|---|---|---|---|
| No. | Porosity (%) | Thickness ($\mu$m) | Before durability test | After durability test |
| 11 | 4 | 100 | NG | NG |
| 12 | 6 | 70 | OK | OK |
| 13 | 7 | 100 | Excellent | Excellent |
| 14 | 10 | 150 | Excellent | Excellent |
| 15 | 15 | 50 | OK | NG |
| 16 | 15 | 250 | Excellent | Excellent |
| 17 | 15 | 400 | OK | OK |
| 18 | 15 | 600 | NG | NG |
| 19 | 30 | 500 | OK | OK |
| 20 | 50 | 500 | OK | NG |

Table 2 shows that the test samples Nos. 12, 13, 14, 16, 17, and 9, in which the porosity of the electrode protective layer 13 lies within a range of 6 to 30%, and the thickness thereof lies within a range of 70 to 500 $\mu$m, especially the test samples Nos. 13, 14, and 15, in which the porosity is between 6 and 15%, and the thickness is between 100 and 250 $\mu$m, have smaller shift in $\lambda$-point and are excellent in output quality before and after the durability test.

The test samples Nos. 11 and 18, in which the porosity of the rode protective layer 13 is smaller than 6%, and the thickness of is greater than 500 $\mu$m, showed great shifts in $\lambda$-point before and after the durability test. This would be because a ratio of a rich-to-lean response time to a lean-to-rich response time of each of the test samples Nos. 11 and 18 during the feedback control of the engine became great on account of decreased diffusion of the oxygen gas in the electrode protective layer 13.

The test samples Nos. 15 and 20, in which the porosity of the electrode protective layer 13 is greater than 30%, and the thickness thereof is smaller than 70 $\mu$m, showed great shifts in $\lambda$-point after the durability test. This would be because the protection of the target gas electrode 11 is too weak to avoid the deterioration of the target gas electrode 11 due to exposure to high temperatures.

Specifically, the formation of the electrode protective layer 13 on the target gas electrode which has the porosity lying in a range of 6 to 30% and the thickness lying in a range of 70 to 500 $\mu$m results in a decreased shift in $\lambda$-point and enables the oxygen sensor element 1 to produce an output accurately over a wide temperature range.

The above embodiment may also be used with a laminated gas sensor element. For example, U.S. Pat. No.

5,573,650, issued on Nov. 12, 1996 to Fukaya et al. teaches a typical laminated sensor element, disclosure of which is incorporated herein by reference.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. An oxygen sensor element comprising:
   an oxygen ion conductive solid electrolyte body;
   a target gas electrode provided on a surface of said solid electrolyte body so as to be exposed to a gas to be measured;
   a reference gas electrode provided on a surface of said solid electrolyte body so as to be exposed to a reference gas;
   an electrode protective layer provided to cover said target gas electrode, said electrode protective layer having a porosity of 6 to 30% and a thickness of 70 to 500 $\mu$m;
   a catalytic layer provided to cover said electrode protective layer, said catalytic layer being made of heat resisting ceramic grains which hold thereon catalytic metal grains whose average grain size is 0.3 to 2.0 $\mu$m, a weight of catalytic metal grains per unit area of said catalytic layer, as defined by projecting the target gas electrode on a plane, is 10 to 200 $\mu$g/cm$^2$; and
   a catalytic protective layer provided to cover said catalytic layer;
   wherein said catalytic protective layer has a porosity of 30 to 60% and a thickness of 20 to 150 $\mu$m.

2. An oxygen sensor element as set forth in claim 1, wherein said catalytic layer has a porosity of 20 to 60% and a thickness of 20 to 150 $\mu$m.

3. An oxygen sensor element as set forth in claim 1, wherein the catalytic metal grains are each made from at least one of Pt, Pd, Rh, and Ru.

4. An oxygen sensor element as set forth in claim 1, wherein said electrode protective layer has a porosity of 6 to 15% and a thickness of 100 to 250 $\mu$m.

5. An oxygen sensor element as set forth in claim 1, wherein said electrode protective layer is formed by a heat resisting metallic oxide made of at least one of alumina, alumina.magnesia spinel, and zirconia.

6. An oxygen sensor element comprising:
   an oxygen ion conductive solid electrolyte body;
   a target gas electrode provided on a surface of said solid electrolyte body so as to be exposed to a gas to be measured;
   a reference gas electrode provided on a surface of said solid electrolyte body so as to be exposed to a reference gas;
   an electrode protective layer provided to cover said target gas electrode;
   a catalytic layer provided to cover said electrode protective layer,
   said catalytic layer being made of heat resisting ceramic grains which hold thereon catalytic metal grains whose average grain size is 0.3 to 2.0 $\mu$m, a weight of catalytic metal grains per unit area of said catalytic layer, as defined by projecting the target gas electrode on a plane, is 10 to 200 $\mu$g/cm$^2$, the heat resisting ceramic grains being each made of Al$_2$O$_3$ which has at least one of a $\gamma$-phase and a $\phi$-phase in crystal structure and to which La$_2$O$_3$ is added, a specific surface of the heat resisting ceramic grains being 50 to 200 m$^2$/g;
   a catalytic protective layer provided to cover said catalytic layer.

7. An oxygen sensor element as set forth in claim 6, wherein an added quantity of La$_2$O$_3$ is 0.5 to 5 mol % for total 100 mol % of Al$_2$O$_3$ and La$_2$O$_3$.

8. An oxygen sensor element as set forth in claim 6, wherein catalytic layer has a porosity of 20 to 60% and a thickness of 20 to 150 $\mu$m.

9. An oxygen sensor element as set forth in claim 6, wherein the catalytic metal grains are each made from at least one of Pt, Pd, Rh, and Ru.

10. An oxygen sensor element as set forth in claim 6, wherein said electrode protective layer has a porosity of 6 to 15% and a thickness of 100 to 250 $\mu$m.

11. An oxygen sensor element as set forth in claim 6, wherein said electrode protective layer is formed by a heat resisting metallic oxide made of at least one of alumina, alumina-magnesia spinel, and zirconia.

12. An oxygen sensor element as set forth in claim 6, wherein said catalytic protective layer has a porosity of 30 to 60% and a thickness of 20 to 150 $\mu$m.

* * * * *